(12) United States Patent
Cavaro et al.

(10) Patent No.: US 8,820,137 B2
(45) Date of Patent: Sep. 2, 2014

(54) METHOD OF DETERMINING VOID RATE BY NONLINEAR ACOUSTIC RESONANCE SPECTROMETRY IN A BIPHASE MEDIUM AND APPLICATION IN A NUCLEAR REACTOR

(75) Inventors: Matthieu Cavaro, Aix en Provence (FR); Cédric Payan, Marseilles (FR)

(73) Assignee: Commissariat a l'Energie Atomique et Aux Energies Alternatives, Paris (FR)

( * ) Notice: Subject to any disclaimer, the term of this patent is extended or adjusted under 35 U.S.C. 154(b) by 0 days.

(21) Appl. No.: 13/696,987

(22) PCT Filed: May 6, 2011

(86) PCT No.: PCT/EP2011/057286
§ 371 (c)(1),
(2), (4) Date: Nov. 28, 2012

(87) PCT Pub. No.: WO2011/141370
PCT Pub. Date: Nov. 17, 2011

(65) Prior Publication Data
US 2013/0205869 A1    Aug. 15, 2013

(30) Foreign Application Priority Data
May 11, 2010  (FR) .................................... 10 53653

(51) Int. Cl.
*G01N 29/036* (2006.01)
*G01N 29/032* (2006.01)
*G01N 29/34* (2006.01)
*G01N 29/44* (2006.01)
*G21C 17/025* (2006.01)

(52) U.S. Cl.
CPC ............ *G01N 29/032* (2013.01); *G01N 29/036* (2013.01); *G01N 29/348* (2013.01); *G01N 2291/02491* (2013.01); *G01N 29/346* (2013.01); *G01N 29/4472* (2013.01); *G21C 17/025* (2013.01); *G01N 2291/02433* (2013.01)
USPC .......................................... 73/19.03; 73/598

(58) Field of Classification Search
USPC ................................ 73/19.03, 597, 598, 599
See application file for complete search history.

(56) References Cited

U.S. PATENT DOCUMENTS 4,567,749 A * 2/1986 Amblard et al. ............. 73/19.03
6,330,827 B1   12/2001 Johnson et al.

OTHER PUBLICATIONS

Koen E-A Van Den Abeele, et al., "On the Quasi-Analytic Treatment of Hysteretic Nonlinear Response in Elastic Wave Propagation", Journal of Acoustical Society of America, Apr. 1997, pp. 1885-1898, vol. 101, No. 4.

(Continued)

*Primary Examiner* — Lisa Caputo
*Assistant Examiner* — Punam Roy
(74) *Attorney, Agent, or Firm* — Baker & Hostetler LLP

(57) ABSTRACT

A method of determining the void rate in a biphase gas/liquid medium, corresponding to the volume fraction of gas corresponding to the presence of bubbles in the liquid medium in a total volume of gas and liquid, comprises: deployment of a bulk elastic wave resonator in contact and coupled acoustically with the biphase medium; measurement by nonlinear resonant ultrasound spectroscopy of the biphase medium comprising the scanning in terms of frequencies and amplitudes in a given range of frequencies and in a given range of amplitudes, of bulk elastic waves emitted and detected at said resonator placed in said medium and leading a set of resonance curves exhibiting maxima; determination of a straight line defined by the set of maxima of said curves and of the slope of said straight line; determination of the void rate on the basis of said slope. The method may be applied to a nuclear reactor.

20 Claims, 3 Drawing Sheets

(56) References Cited

OTHER PUBLICATIONS

K. E.-A. Van Den Abeele, et al., "Nonlinear Elastic Wave Spectroscopy (NEWS) Techniques to Discert Material damage, Part II: Single-Mode Nonlinear Resonance Acoustic Spectroscopy", Res Nondestr Eval, 2000, pp. 31-42, vol. 12, Springer-Verlag New York Inc.

A. Bouakaz, et al., "Dynamique de la Microbulle", Chapter on Contrast Echography, 2007, 2 pages, Springer.

M. Minnaert, "On Musical Air-Bubbles and the Sounds of Running Water", Phil. Mag, 1933, pp. 235-248, vol. 16, No. 7.

M. Cavaro, et al., "Towards In-service Acoustic Characterization of Gaseous Microbubbles Applied to Liquid Sodium", 2009 1st International Conference on Advancement in Nuclear Instrumentation, Measurement Methods and Their Applications, Jun. 7-10, 2009, pp. 1-6, IEEE Piscataway, NJ, USA, XP031704404.

C. Payan, et al., "Applying Nonlinear Resonant Ultrasound Spectroscopy to Improving Thermal Damage Assessment in Concrete", The Journal of the Acoustical Society of America, Mar. 13, 2007, pp. 125-130, vol. 121, No. 4, American Institute of Physics for the Acoustical Society of America, New York, NY, USA, XP012096561.

Koen E-A. Van Den Abelle, et al., Micro-Damage Diagnostics Using Nonlinear Elastic Wave Spectroscopy (NEWS), Jun. 1, 2001, pp. 239-248, vol. 34, No. 4, NDT & E International Butterworth-Heinemann, Oxford, GB, XP004292762.

Marie Muller, et al., "Nonlinear Resonant Ultrasound Spectroscopy (NRUS) Applied to Damage Assessment in Bone", The Journal of the Acoustical Society of America, Jan. 1, 2005, pp. 3946-3952, vol. 118, No. 6, American Institute of Physics for the Acoustical Society of America, New York, NY, USA, XP012073507.

* cited by examiner

METHOD OF DETERMINING VOID RATE BY NONLINEAR ACOUSTIC RESONANCE SPECTROMETRY IN A BIPHASE MEDIUM AND APPLICATION IN A NUCLEAR REACTOR

CROSS-REFERENCE TO RELATED APPLICATIONS

This application is a National Stage of International patent application PCT/EP2011/057286, filed on May 6, 2011, which claims priority to foreign French patent application No. FR 1053653, filed on May 11, 2010, the disclosures of which are incorporated by reference in their entirety.

FIELD OF THE INVENTION

The field of the invention is that of the determination (or characterization) of so-called void rate in a biphase gas/liquid medium, corresponding to the determination (or characterization) of volume of gas bubbles within a volume of liquid.

BACKGROUND

There exist numerous fields in which the determination of void rate is of interest and notably in fields as varied as the nuclear industry, the food-processing industry, the oil industry, the chemical industry, cryogenic applications, medicine (imaging and problems of decompression sickness) or else the field of underwater acoustics.

More precisely in the nuclear field, and notably for the fourth generation of fast neutron nuclear reactor (or "FBR" standing for "Fast Breeder Reactor"), the SFR ("Sodium Fast Reactor") reactor appears very promising.

This family of reactors presents several challenges, in particular from the point of view of improving monitoring. Among the checks to be performed in the vessel of SFRs, there is one which was not taken into account within the framework of the development and exploitation of the Phenix and Superphenix SFRs: measurement of the continuous engassment of the primary sodium.

More precisely, "engassment" is defined as the presence of gas in a liquid (or a solid) in the form of bubbles (free gas). The gases dissolved in the liquid phase are not considered as belonging to the gas volume but as belonging to the liquid volume, when evaluating a so-called void rate.

Generally, an "FBR" is a reactor whose core is not moderated. Fast spectrum operation presents a certain number of advantages such as the possibility of implementing supergeneration or transmutation of minor actinides but it requires the use of a heat-exchanging fluid with low neutron capture cross-section such as liquid sodium. FIG. 1 illustrates the diagram of such a type of reactor according to the known art.

Indeed, liquid sodium possesses the properties expected of a heat-exchanging fluid, namely good thermal properties, low noxiousness, low cost etc. Its main drawbacks are its reactivity to air and especially to water and its opacity which renders the inspectability of the reactors more difficult than in water.

The gas present in free form in the liquid sodium of SFRs can have diverse origins and be of diverse kinds. There exist two possible sites of existence of gas bubbles in the sodium: the primary circuit (the main vessel in which the core is immersed) and the secondary circuit (circuit of the exchangers).

SFR type reactors use liquid sodium as heat-exchanging fluid. This fluid phase, present in the primary vessel of the reactor, circulates through the core, the pumps and the exchangers so as to extract the heat emanating from nuclear fission. This sodium pool is surmounted by a cover gas, also called a pile headspace (generally argon).

Ideally, this liquid sodium is perfectly pure and monophase. In reality, this is not the case: in addition to comprising a few impurities and dissolved gases, the sodium continuously comprises bubbles of free gas.

This continuous engassment nevertheless presents several negative consequences and notably the presence of bubbles in a liquid which very greatly modifies its acoustic properties (speed, attenuation, diffusion, nonlinear properties, etc.).

The deployment of acoustic measurement procedures for continuous monitoring, which is performed at the nominal power (measurement of the displacement of assembly heads, ultrasound thermometry based on flight time measurement), or the periodic checks operating in the shutdown regime (ultrasound telemetry, surface metrology, volume checking, etc.) requires a knowledge of an order of magnitude of the attenuation coefficients, so as to prove a priori that the amplitude of the signal is sufficient, as well as an order of magnitude of the lack of homogeneity of the spatial distribution, to prove that the speed calibrations carried out some distance from the effective measurement point, remain usable.

The aforementioned measurements thus necessarily demand a knowledge of the void rate value, backed up if appropriate with certain data relating to the histogram of the radii of the bubbles (at least the bounds).

If the evaluated void rate is not in itself directly deleterious in relation to the operation of the core, it is indirectly so if it participates in the generation of gas pockets at high points of the submerged structures.

The characterization of the continuous primary engassment in a reactor can thus serve as input data for trials or calculations for the formation and relaxation of these gas pockets. It must be pointed out that the abrupt relaxation of accumulated pockets of gas formed part of the scenarios envisaged for explaining the series of emergency shutdowns on reactors that has operated in the past.

Moreover, the continuous tracking of the engassment rate seems necessary for controlling the non-exceeding of several thresholds and notably:
 the neutronic perturbation threshold (a priori too high to be attainable under the normal operating conditions of the reactor: of the order of several percent);
 the blinding threshold of the systems for measuring activity in the pile headspace.

Currently, in order to determine void rates, optical techniques are usable in translucent liquids, but these are no longer transposable into opaque media such as liquid sodium.

Linear acoustic techniques based on the attenuation or the spreading of an acoustic wave are usable but exhibit an ambiguity—between resonant bubble and big bubble—which is impossible to resolve without a priori knowledge about the bubble cloud. For certain ranges of void rate and of bubble sizes, speed measurements are sometimes implemented to determine the void rate.

In this context and to address the problematic issue of determining void rate applicable in a gas/liquid biphase non-translucent medium and notably of possibly very low void rate, typically of the order of $10^{-6}$ to $10^{-8}$, the present invention proposes to exploit the so-called "NRUS" procedure, frequently encountered in the literature under the acronym standing for "Nonlinear Resonant Ultrasound Spectroscopy". It is a nonlinear acoustics technique used mainly in the field of the acoustics of solids.

Generally, a mechanical system possesses resonant modes, all associated with a natural resonant frequency. As a general rule, these resonant frequencies are dependent on the geometric characteristics and the speed of the waves in the medium constituting the system. Now, the speed in a medium is dependent on its density and its compressibility. In the case of nonlinear acoustics, the modulus of elasticity is not constant and is dependent on the applied stress. It follows from this that the resonant frequency of a nonlinear mechanical system varies as a function of the applied stress and therefore of the acoustic excitation amplitude.

Nonlinear resonant ultrasound spectroscopy consists in observing this type of phenomenon by exciting the mechanical system considered while performing a frequency scan at various amplitudes. A shift between the resonance peaks then appears.

The authors K. Van Den Abeele et al. have notably proposed in the article, "*On the quasi-analytic treatment of hysteretic nonlinear response in elastic wave propagation*"—J. Acoust. Soc. Am. 101 (4), April 1997 1885-1898, the following model of the nonlinear modulus of elasticity:

$$K\left(\varepsilon, \frac{\partial \varepsilon}{\partial t}\right) = K_0\left[1 + \beta\varepsilon + \alpha\left(\Delta\varepsilon + \text{sign}\left(\frac{\partial \varepsilon}{\partial t}\right)\varepsilon\right)\right]$$

With $\beta$ the conventional nonlinear parameter and $\alpha$ the nonconventional nonlinear parameter, $\epsilon$ being the instantaneous strain and $\Delta\epsilon$ the amplitude of the strain.

If $f_0$ is the linear resonant frequency of a mechanical system (measured at low amplitudes) and f the resonant frequency measured for waves of larger amplitude and by considering the parameter $\alpha$ to be strongly predominant over the parameter $\beta$, this seeming to be confirmed by the experiments described in the articles by K. Van Den Abeele et al.—*Nonlinear ElasticWave Spectroscopy (NEWS) Techniques to Discern Material Damage, Part I: Nonlinear Wave Modulation Spectroscopy (NWMS), Part II: Single Mode Nonlinear Resonance Acoustic Spectroscopy*—Res Nondestr Eval (2000) 12: 17-42 or *Micro-damage diagnostics using nonlinear elastic wave spectroscopy (NEWS)*—NDT&E International 34 (2001) 239-248, the following relation is obtained:

$$\frac{f_0 - f}{f_0} \approx \alpha\Delta\varepsilon$$

The NRUS procedure consists in measuring a frequency shift which turns out to be proportional to the nonconventional nonlinear parameter by frequency scanning. The frequency shift observed is a fast dynamics phenomenon.

The field of nonlinear elasticity of materials and notably of materials such as rocks has already been explored for a long time, but the technique today called NRUS began to be studied in depth and exploited for the characterization of media really toward the middle of the 1990s.

An NRUS procedure for characterizing damage to materials has notably been described in U.S. Pat. No. 6,330,827. This patent entails applying the NRUS procedure and deducing, from the frequency shift, damage to the material tested.

The article by M. Muller et al.—*Nonlinear resonant ultrasound spectroscopy (NRUS) applied to damage assesment in bone*—J. Acous. Soc. Am., Vol. 118(6), p. 3946-3952, December. 2005, presents another interesting application of the NRUS technique: the detection of fractures in bones. Spectroscopy of a healthy bone exhibits a constancy of the resonant frequency whereas a fractured bone exhibits a frequency shift.

The use of the RNUS procedure for detecting defects in materials has also been described in the article by Payan et al.: "Applying nonlinear resonant ultrasound spectroscopy to improving thermal damage assessment in concrete", 13 Mar. 2007.

Thus, according to the known art, the procedures of NRUS type are employed to detect defects constituting discontinuities which are the source of nonlinearities in solid media.

Concerning biphase media, the inventors have mentioned in a publication: Cavaro M. ET AL: "Towards in-service acoustic characterization of gaseous microbubbles applied to liquid sodium" 2009 1ST INTERNATIONAL CONFERENCE ON ADVANCEMENTS IN NUCLEAR INSTRUMENTATION MEASUREMENTS METHODS AND THEIR APPLICATIONS" XP031704404, the possibility of using acoustic nonlinearities notably to detect bubble sizes by virtue of the presence of two acoustic wave transducers emitting in a biphase medium, a first transducer emitting an acoustic wave at a fixed first frequency $f_1$, a second transducer emitting an acoustic wave at a variable second frequency $f_2$. The bubbles present in the bubbly medium generate an acoustic wave with a frequency difference $\Delta(f_1-f_2)$ detected by a hydrophone, frequency scanning thus making it possible to detect various frequency differences and thus various sizes of bubble.

In this article, the authors mention the possibility of using the procedure of RNUS type but without proposing any solution making it possible to implement such a procedure and to do so in order to determine a void rate in a biphase medium.

SUMMARY OF THE INVENTION

This is why, in this context the subject of the present invention is a method of determining void rate exploiting the use of a bulk elastic wave resonator.

More precisely the subject of the present invention is a method of determining the void rate in a biphase gas/liquid medium, corresponding to the volume fraction of gas corresponding to the presence of bubbles in the liquid medium in a total volume of gas and liquid, characterized in that it comprises the following steps:
  the deployment of a bulk elastic wave resonator in contact and coupled acoustically with the biphase medium;
  the measurement by nonlinear resonant ultrasound spectroscopy of the biphase medium comprising the scanning in terms of frequencies and amplitudes of acoustic excitation in a given range of frequencies and in a given range of amplitudes, of bulk elastic waves emitted and detected at said resonator and leading to the obtaining of a set of resonance curves exhibiting maxima;
  the determination of a straight line defined by the set of maxima of said resonance curves for different excitation amplitudes and of the slope ($\alpha$) of said straight line;
  the determination of the void rate on the basis of said slope.

According to a variant of the invention, the method comprises a prior step of determining the resonant frequency of said gas bubbles.

According to a variant of the invention, the prior step of determining the size of the biggest bubbles present—so as to choose a resonator whose resonant frequency is appropriate—is performed by optical measurement.

According to a variant of the invention, the bubbles having a radius of the order of a hundred microns, the frequency scan by the implementation of the NRUS procedure is performed below 33 KHz, the resonant frequency of 100-micron air bubbles in water.

According to a variant of the invention, the bulk wave resonator comprises a first metallic plate connected to an emitter, a second metallic plate connected to a receiver.

According to a variant of the invention, the first plate is connected to a transducer.

According to a variant of the invention, the second plate is connected to a hydrophone.

According to a variant of the invention, the bulk wave resonator is of Helmholtz type.

According to a variant of the invention, the liquid is a metal in the liquid state.

According to a variant of the invention, the liquid is sodium.

The subject of the invention is also the application of the method of determining the void rate in a biphase gas/liquid medium according to the invention, in a nuclear reactor so as to determine a void rate in a heat-exchanging liquid.

According to a variant of the invention, the nuclear reactor is a fast neutron reactor.

According to a variant of the invention, the resonator is of plate type and is placed in the primary circuit of the reactor.

According to a variant of the invention, the resonator is of Helmoltz resonator type and is placed branched off from the primary circuit or from the secondary circuit of the reactor.

BRIEF DESCRIPTION OF THE DRAWINGS

The invention will be better understood and other advantages will become apparent on reading the nonlimiting description which follows and by virtue of the appended figures among which.

DETAILED DESCRIPTION

Figure 1:
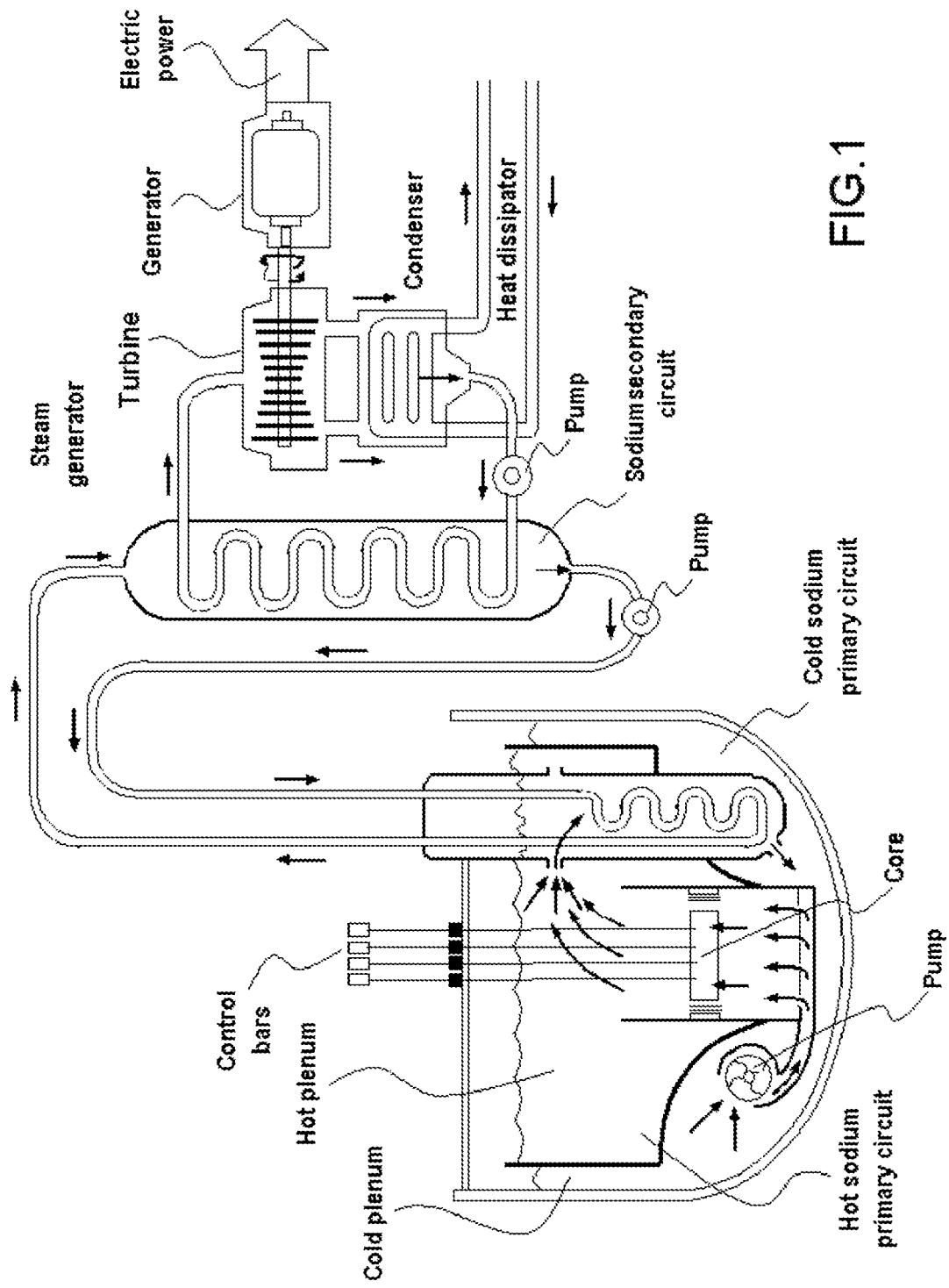
FIG. 1 illustrates the diagram of a nuclear reactor comprising primary and secondary circuits according to the known art.

The method of determining void rate of the invention is applied in a liquid/gas biphase medium, the liquid possibly being notably a heat-exchanging fluid laden with gas bubbles or indeed with air bubbles. The bubbles present in said liquid generate acoustics-related nonlinearities and the nonlinearity coefficient is determined via resonant spectroscopy, that is to say a scan in terms of frequency and amplitude. The nonlinearities related to the presence of bubbles in the liquid medium induce a frequency shift. It is this shift which makes it possible to deduce a nonlinearity coefficient.

According to the known art, the problematic issue of the propagation of an acoustic wave in a bubbly liquid is often treated in a linear manner. This approach is valid for low-amplitude oscillations. When it is applicable, it makes it possible moreover to establish a good approximation of the speeds, attenuations, diffusions etc. in biphase media.

Like any mechanical system, a bubble exhibits a resonant frequency. Let us consider a spherical air bubble in a volume of water. This system possesses, on account of the respective compressibilities of the air and of the water, an infinity of degrees of freedom and therefore an infinity of natural modes of oscillation.

Nonetheless an air bubble in water possesses a particular feature: the presence of a fundamental radial resonance lying at a frequency corresponding to wavelengths in air and in water which are very large compared with the size of the bubble. This fundamental radial mode is in general the only one considered when one speaks of resonance of bubbles since it is very strongly predominant from an energy point of view.

It is possible to envisage just the spherically symmetric volume pulsations of the bubbles (mode 0) only when k.a<<1. Only mode 0 gives rise to volume variations as described in the article by A. Bouakaz, P. Palanchon, N. de Jong—*Dynamique de la microbulle [Dynamics of the microbubble]— Chapter on Contrast Echography*, Springer, 2007.

The frequency corresponding to the fundamental mode of resonance of a bubble is named the Minnaert frequency as described in the article—*On musical air bubbles and the sound of running water*—Phil. Mag., 16(7), p. 235 to 248, 1933. Minnaert resonance involves large acoustic wavelengths compared with the radius of the bubbles. The vibratory phenomenon of the bubbles in a fluid can then be considered to be a harmonic oscillator model (mass-spring system, the mass being constituted by the fluid surrounding the bubble and the spring by the compressible gas of the bubble).

The Minnaert model, the oldest describing the resonant frequency of a bubble of radius R is as follows (let us point out that in many cases, this simple linear model suffices):

$$f_{res} = \frac{1}{2\pi R}\sqrt{\frac{3\gamma p_0}{\rho_l}}$$

with:

γ=isentropic exponent of the gas (no unit)
$p_0$=static pressure (Pa)
$p_l$=density of the liquid (kg·m$^{-3}$)
For the air-water system, this gives a coefficient of:

frequency*radius=3.29 SI

This therefore constitutes the criterion for choosing the frequency of the resonator.

The presence of bubbles will then cause the resonant frequency of the resonator to decrease, in a manner dependent on the void rate. Having no a priori knowledge of the void rate (since one is seeking to measure it), it must therefore be performed from 0 to the frequency calculated previously+ about 20%.

Example of Determining Rate of Air Bubbles in an Aqueous Medium:

For a cloud of bubbles therefore the bubbles exhibit a radius of less than 100 microns, the resonant frequency of the biggest bubbles is 333 kHZ. A much smaller resonant frequency of the resonator will be chosen: (divided by about 5) i.e. about 6 kHz.

The frequency scan by implementing the NRUS procedure can thus be performed from 0 to 7.2 kHz (6 kHz+20%).

Figure 2:
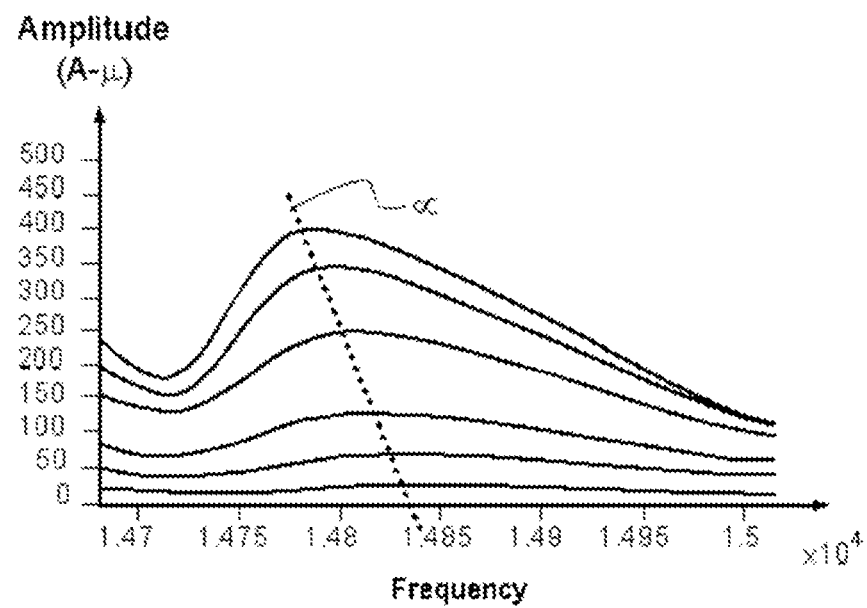
FIG. 2 illustrates a set of curves established in the method of the invention making it possible to define a void rate.

By way of illustration of the method of the invention, FIG. 2 shows diagrammatically how to determine via a set of curves giving the amplitude of the bulk waves analyzed according to a frequency scan, and via the maxima of said curves, the coefficient α making it possible to determine a void rate of the medium, (measurements performed by virtue of a plate resonator whose resonant frequency lies at round about 15 kHz).

It should be noted that the method of the invention makes it possible to access a wide range of measurable void rates, makes it possible to avoid measurement ambiguity in contradistinction to the linear procedures and, the nonlinearities of the bubbles very strongly dominating all the other nonlinearities present (electronic, water, etc.), the latter then become negligible.

Figure 3:
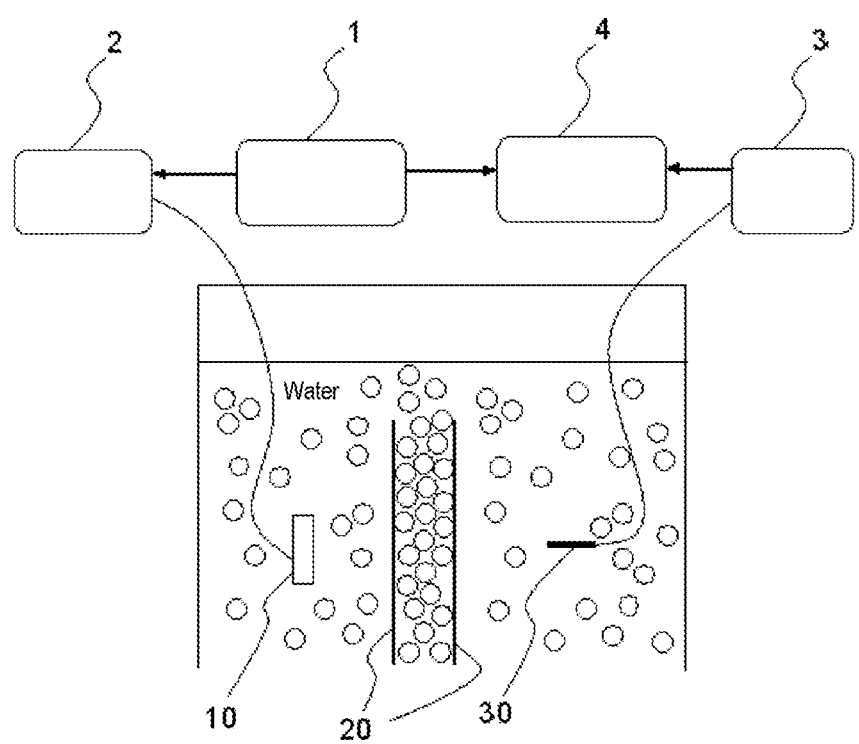
FIG. 3 illustrates a first exemplary device comprising a bulk elastic wave resonator of plate type, used in the method of the invention.

First Exemplary Application of a Device Allowing the Implementation of the Method of the Invention, Positioned in a First Location of a Nuclear Reactor Primary Circuit The method of the present invention makes it possible to determine the rate of bubbles present in a liquid sodium heat-exchanging fluid. A biphase fluid sheet is set resonating by virtue of the use of a resonator consisting of two plates, as illustrated in FIG. 3, that may typically be spaced a few tens of millimeters apart. A first plate is connected to an emitter, a second plate is connected to a hydrophone. The emitter is a transducer emitting for example at 100 kHz.

A signals generator 1 feeds a power amplifier 2, connected to a transducer capable of generating bulk elastic waves 10, the bulk wave resonator is formed by two plates 20.

On output the bulk waves are sensed by a low-frequency hydrophone 30, linked for analysis to a charge amplifier 3, coupled to an oscilloscope 4.

Second Exemplary Application of a Device Allowing the Implementation of the Method of the Invention, Positioned in a Second Location Branching off from the Primary or Secondary Circuit of a Nuclear Reactor.

A resonator of Helmoltz type is defined in the following manner:
1—a closed cavity of volume V which communicates with the exterior by way of a small tube of length L and of cross-section A;
2—the aforementioned dimensions are small compared with the length of the acoustic waves considered.

A Helmholtz resonator makes it possible to obtain an acoustic resonance at the resonant frequency of the Helmholtz resonator defined by:

$$f = \frac{c}{2\pi}\sqrt{\frac{A}{VL}}$$

With A, V and L the aforementioned dimensions and c the acoustic speed in the medium considered.

Figure 4:
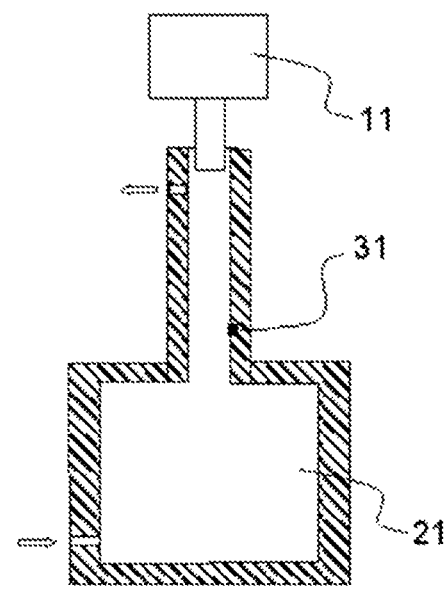
FIG. 4 illustrates a second exemplary device comprising a Helmholtz-type bulk elastic wave resonator used in the method of the invention.

As illustrated in FIG. 4, an emitter 11 is placed at an end of the resonator of Helmoltz type, so as to generate bulk waves, received at acoustic receivers 31 after resonance in the cavity 21.

The invention claimed is:

1. A method of determining a void rate in a biphase gas/liquid medium, the void rate corresponding to a fraction of a volume of gas corresponding to gas bubbles in the gas/liquid medium to a total volume of gas and liquid in the gas/liquid medium, the method comprising:
defining a size of the largest gas bubbles in the gas/liquid medium by optical measurement;
deploying a bulk elastic wave resonator in contact and coupled acoustically with the biphase gas/liquid medium;
measuring, by nonlinear resonant ultrasound spectroscopy of the biphase gas/liquid medium in terms of frequencies and amplitudes of acoustic excitation in a given range of frequencies based on the size of the largest gas bubbles and in a given range of amplitudes, bulk elastic waves emitted and detected at said resonator, resulting in a set of resonance curves exhibiting maxima;
determining a straight line defined by the maxima of said set of resonance curves having different excitation amplitudes;
determining a slope of said straight line; and
determining the void rate based on said slope.

2. The method of determining the void rate in the biphase gas/liquid medium as claimed in claim 1, further comprising determining a resonant frequency of said gas bubbles.

3. The method of determining the void rate in the biphase gas/liquid medium as claimed in claim 1, wherein:
the gas bubbles have a radius on the order of a hundred microns,
the given range of frequencies is below 33 kHz,
the liquid medium is water, and
the gas bubbles are air bubbles.

4. The method of determining the void rate in the biphase gas/liquid medium as claimed in claim 1, wherein the bulk elastic wave resonator is placed in said biphase gas/liquid medium, and the bulk elastic wave resonator comprises a first metallic plate connected to an emitter and a second metallic plate connected to a receiver.

5. The method of determining the void rate in the biphase gas/liquid medium as claimed in claim 4, wherein the first plate is connected to a transducer.

6. The method of determining the void rate in the biphase gas/liquid medium as claimed in claim 4, wherein the second plate is connected to a hydrophone.

7. The method of determining the void rate in the biphase gas/liquid medium as claimed in claim 4, wherein the first metallic plate is a front face of the emitter and the second metallic plate is a front face of the receiver.

8. The method of determining the void rate in the biphase gas/liquid medium as claimed in claim 1, wherein the bulk elastic wave resonator is of Helmholtz type, and the biphase medium is introduced into said bulk elastic wave resonator.

9. The method of determining the void rate in the biphase gas/liquid medium as claimed in claim 1, wherein the liquid is a metal in a liquid state.

10. The method of determining the void rate in the biphase gas/liquid medium as claimed in claim 9, wherein the metal is sodium.

11. A nuclear reactor configured to apply the method of determining the void rate in the biphase gas/liquid medium as claimed in claim 1.

12. The nuclear reactor as claimed in claim 11, wherein the resonator is of plate type, and the resonator is placed within the liquid of sodium type of a primary circuit of the nuclear reactor.

13. The nuclear reactor as claimed in claim 11, wherein the resonator is of Helmholtz resonator type, and the resonator is placed branched off from a primary or secondary circuit of the nuclear reactor.

14. A fast neutron reactor configured to apply the method of determining the void rate in the biphase gas/liquid medium as claimed in claim 1.

15. The method of determining the void rate in the biphase gas/liquid medium as claimed in claim 1, wherein each resonance curve in the set of resonance curves exhibits a single maximum.

16. A method of determining a void rate in a biphase gas/liquid medium, the void rate corresponding to a fraction of a volume of gas corresponding to gas bubbles in the gas/liquid medium to a total volume of gas and liquid in the gas/liquid medium, the method comprising:

deploying a bulk elastic wave resonator in the biphase gas/liquid medium, the bulk elastic wave resonator comprising a first metallic plate connected to a transducer and a second metallic plate connected to a receiver;

measuring, by nonlinear resonant ultrasound spectroscopy of the biphase gas/liquid medium in terms of frequencies and amplitudes of acoustic excitation in a given range of frequencies and in a given range of amplitudes, bulk elastic waves emitted and detected at said resonator, resulting in a set of resonance curves exhibiting maxima;

determining a straight line defined by the maxima of said set of resonance curves having different excitation amplitudes;

determining a slope of said straight line; and determining the void rate based on said slope.

17. The method of determining the void rate in the biphase gas/liquid medium as claimed in claim 16, wherein the first metallic plate is a front face of the resonator and the second metallic plate is a front face of the receiver.

18. The method of determining the void rate in the biphase gas/liquid medium as claimed in claim 16, wherein the bulk elastic wave resonator is of Helmholtz type.

19. A fast neutron reactor configured to determine a void rate in a biphase gas/liquid medium, the void rate corresponding to a fraction of a volume of gas corresponding to gas bubbles in the gas/liquid medium to a total volume of gas and liquid in the gas/liquid medium, the fast neutron reactor being configured to determine the void rate in the biphase gas/liquid medium by:

deploying a bulk elastic wave resonator in contact and coupled acoustically with the biphase gas/liquid medium;

measuring, by nonlinear resonant ultrasound spectroscopy of the biphase gas/liquid medium in terms of frequencies and amplitudes of acoustic excitation in a given range of frequencies and in a given range of amplitudes, bulk elastic waves emitted and detected at said resonator, resulting in a set of resonance curves exhibiting maxima;

determining a straight line defined by the maxima of said set of resonance curves having different excitation amplitudes;

determining a slope of said straight line; and determining the void rate based on said slope.

20. The fast neutron reactor as claimed in claim 19, wherein the resonator is placed within a primary circuit of the fast neutron reactor.

* * * * *